United States Patent
Itagaki et al.

(10) Patent No.: US 6,852,871 B2
(45) Date of Patent: Feb. 8, 2005

(54) METHOD FOR PRODUCING OPTICALLY ACTIVE SALICYLALDIMINE COPPER COMPLEX

(75) Inventors: Makoto Itagaki, Katano (JP); Koji Hagiya, Ibaraki (JP)

(73) Assignee: Sumitomo Chemical Company Limited, Osaka (JP)

( * ) Notice: Subject to any disclaimer, the term of this patent is extended or adjusted under 35 U.S.C. 154(b) by 29 days.

(21) Appl. No.: 10/457,514

(22) Filed: Jun. 10, 2003

(65) Prior Publication Data
US 2003/0233003 A1 Dec. 18, 2003

(30) Foreign Application Priority Data

Jun. 12, 2002 (JP) ........................... 2002-171033

(51) Int. Cl.[7] .................................................. C07F 1/08
(52) U.S. Cl. ............................................... 556/33
(58) Field of Search ............................................ 556/33

(56) References Cited

U.S. PATENT DOCUMENTS

| | | | |
|---|---|---|---|
| 4,029,683 A | 6/1977 | Aratani et al. | |
| 4,029,690 A | 6/1977 | Aratani et al. | |

FOREIGN PATENT DOCUMENTS

| | | | |
|---|---|---|---|
| EP | 0023075 A1 | 1/1981 | |
| EP | 1120401 A2 | 8/2001 | |
| EP | 1120402 A2 | 8/2001 | |
| EP | 1120402 A3 | 5/2002 | |
| GB | 1455189 | 11/1976 | |
| JP | 53-43955 | 11/1978 | |
| JP | 59-225194 | * 12/1984 | |
| JP | 2002-241356 | * 8/2002 | |

OTHER PUBLICATIONS

"Catalytic asymmetric synthesis of cyclopropane–carboxylic acids: an application of chiral copper carbenoid reaction", Tadatoshi Aratani, Pur & Appl. Chem., vol. 57, No. 12, pp. 1839–1844, 1985.

* cited by examiner

Primary Examiner—Porfirio Nazario-Gonzalez
(74) Attorney, Agent, or Firm—Sughrue Mion, PLLC

(57) ABSTRACT

There is provided a method for producing an optically active salicylaldimine copper complex, which method is characterized in that an optically active amino alcohol compound represented by the following formula (1) is reacted with copper hydroxide (II) in an organic solvent:

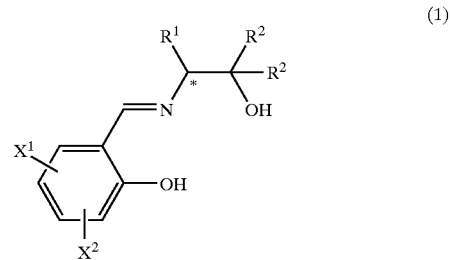

(1)

wherein $R^1$ and $R^2$ which are the same or different, each represent lower alkyl groups and the like which may be substituted, $X^1$ and $X^2$ which are the same or different, each represent a hydrogen atom, lower alkyl groups and the like, and the symbol * designates an asymmetric carbon atom.

5 Claims, No Drawings

METHOD FOR PRODUCING OPTICALLY ACTIVE SALICYLALDIMINE COPPER COMPLEX

FIELD OF THE INVENTION

The present invention relates to a method for producing an optically active salicylaldimine copper complex.

BACKGROUND OF THE INVENTION

Optically active salicylaldimine copper complexes are known to be useful as catalysts for a variety of organic synthetic reactions. For example, an optically active salicylaldimine copper complex which is obtained by reacting optically active N-salicylidene-2-amino-1,1-di(2-isopropoxyphenyl)-1-propan-ol with copper acetate (II) is known to be useful as a catalyst for asymmetric cyclopropanation (Japanese Examined Patent Publication JP-B2 S53-43955). In the reaction of the optically active N-salicylidene-2-amino-1,1-di(2-ispropoxyphenyl)-1-propanol with the copper acetate (II), acetic acid is by-produced as the reaction progresses. Since this byproduct acetic acid may inhibit the catalytic reaction or may corrode a reaction apparatus, it is necessary to conduct an operation of removing the by-produced acetic acid by neutralization using bases such as sodium hydrogen carbonate.

SUMMARY OF THE INVENTION

According to the present invention, the undesirable byproduct is not produced and an optically active salicylaldimine copper complex can be readily produced.

Thus, the present invention provides:

a method for producing an optically active salicylaldimine copper complex, comprising reacting a copper hydroxide (II) with an optically active salicylaldimine compound of formula (1):

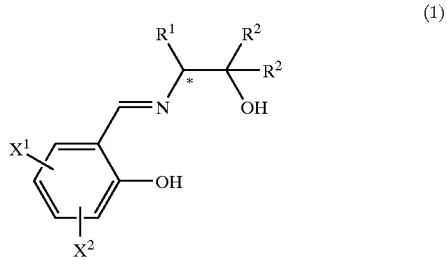

(1)

wherein $R^1$, and $R^2$ are the same or different and independently represent a substituted or unsubstituted lower alkyl group, a substituted or unsubstituted aryl group, or a substituted or unsubstituted aralkyl group, $X^1$ and $X^2$ are the same or different and independently represent a hydrogen atom, a substituted or unsubstituted lower alkyl group, a lower alkoxy group, a nitro group, a lower alkoxycarbony group or a halogen atom, and the symbol * designates an asymmetric carbon atom, provided that $X^1$ and $X^2$ on adjacent carbon atoms, together with the carbon atoms to which they are boded, form a benzene ring, in an organic solvent.

DETAILED DESCRIPTION OF THE INVENTION

First, a description will be made on an optically active salicylaldimine compound of formula (1).

Examples of substituted or unsubstituted lower alkyl groups represented by $R^1$ or $R^2$ include, for example, straight-chain or branched-chain alkyl groups having 1 to 4 carbon(s) such as a methyl group, an ethyl group, a n-propyl group, an isopropyl group, a n-butyl group, an isobutyl group, a sec-butyl group and a tert-butyl group.

Examples of the substituted alkyl groups represented by $R^1$ or $R^2$ include, for example, an alkyl group substituted with a lower alkoxy group such as a methoxy group or an ethoxy group, or with a halogen atom such as a fluorine atom or a chlorine atom. Examples of the substituted alkyl group include, for example, a chloromethyl group, a fluoromethyl group, a trifluoromethyl group, a methoxymethyl group and the like.

Examples of the substituted or unsubstituted aryl group represented by $R^1$ or $R^2$ include include, for example, an unsubstituted aryl group such as a phenyl group, a naphthyl group or the like, and the aryl group substituted with at least one group selected from a C1–10 alkyl group (e.g. methyl, ethyl, n-propyl, i-propyl, n-butyl, t-butyl, n-pentyl, n-hexyl, n-heptyl, n-octyl, n-nonyl, and n-decyl groups), a C1–10 alkoxy group (e.g. methoxy, ethoxy, propoxy, butoxy, pentyloxy, hexyloxy, heptyloxy, octyloxy, nonyloxy, decyloxy groups and the like), a halogen atom (e.g. fluorine, chlorine, bromine, and iodine), and a nitro group.

Examples of the substituted aryl group include, for example, 2-methoxyphenyl group, 2-n-butoxy-5-tert-butylphenyl group, 2-octyloxy-5-tert-butylphenyl group, and the like.

Examples of substituted or unsubstituted aralkyl group include, for example, the aforementioned alkyl group (e.g. C1–4 alkyl group) substituted with the substituted or unsubstituted aryl group as described above (e.g. benzyl group, 2-methoxybenzyl group and the like).

Examples of the substituted or unsubstituted lower alkyl groups represented by $X^1$ or $X^2$ include, for example, straight-chain or branched-chain alkyl groups having 1 to 4 carbon(s) such as a methyl group, an ethyl group, a n-propyl group, an isopropyl group, a n-butyl group, an isobutyl group, a tert-butyl group, and halogen-substituted alkyl group such as a halogen(e.g. chlorine, fluorine and the like)-substituted alkyl group such as a trichloromethyl group, a trifluoromethyl group and the like.

Examples of the lower alkoxy groups represented by $X^1$ or $X^2$ include, for example, a straight-chain or branched chain alkoxy group having 1 to 4 carbon(s) such as a methoxy group, an ethoxy group, a n-propoxy group, an isopropoxy group, a n-butoxy group, an isobutoxy group and a tert-butoxy group.

Examples of the lower alkoxycarbonyl group represented by $X^1$ or $X^2$ include, for example, lower alkoxy group (e.g. methoxycarbonyl group, ethoxycarbonyl group or the like).

Examples of the halogen atom represented by $X^1$ or $X^2$ include a fluorine atom, a chlorine atom, a bromine atom and the like.

Examples of the groups formed by $X^1$ and $X^2$ on adjacent carbon atoms together with the carbon atoms to which they are bonded include, for example, a benzene ring and the like.

Examples of the salicylaldimine compounds (1) include: for example,
(R)-N-salicylidene-2-amino-1,1-diphenyl-1-propanol,
(R)-N-(5-nitrosalicylidene)-2-amino-1,1-diphenyl-1-propanol,
(R)-N-(3,5-dinitrosalicylidene)-2-amino-1,1-diphenyl-1-propoanol, (R)-N-(5-chlorosalicylidene)-2-amino-1,1-diphenyl-1-propanol,
(R)-(3,5-dichlorosalicylidene)-2-amino-1,1-diphenyl-1-propanol,
(R)-N-(3-fluorosalicylidene)-2-amino-1,1-diphenyl-1-propanol,
(R)-N-(3-bromosalicylidene)-2-amino-1,1-diphenyl-1-propanol,
(R)-N-(3-methylsalicylidene)-2-amino-1,1-diphenyl-1-propanol,
(R)-N-(3-trifluoromethylsalicylidene)-2-amino-1,1-diphenyl-1-propanol,
(R)-N-(5-trifluoromethylsalicylidene)-2-amino-1,1-diphenyl-1-propanol,
(R)-N-(3-methoxysalicylidene)-2-amino-1,1-diphenyl-1-propanol,
(R)-N-salicylidene-2-amino-1,1-di(2-methoxyphenyl)-1-propanol, (R)-N-(5-nitrosalicylidene)-2-amino-1,1-di(2-methoxyphenyl)-1-propanol,
(R)-N-(3,5-dinitrosalicylidene)-2-amino-1,1-di(2-methoxy-phenyl)-1-propanol,
(R)-N-(5-chlorosalicylidene)-2-amino-1,1-di(2-methoxy-phenyl)-1-propanol,
(R)-N-(3,5-dichlorosalicylidene)-2-amino-1,1-di(2-methoxy-phenyl)-1-propanol,
(R)-N-(3-fluorosalicylidene)-2-amino-1,1-di(2-methoxyphenyl)-1-propanol,
(R)-N-(3-bromosalicylidene)-2-amino-1,1-di(2-methoxyphenyl)-1-propanol,
(R)-N-(3-methylsalicylidene)-2-amino-1,1-di(2-methoxyphenyl)-1-propanol,
(R)-N-(3-trifluoromethylsalicylidene)-2-amino-1,1-di(2-methoxyphenyl)-1-propanol,
(R)-N-(5-trifluoromethylsalicylidene)-2-amino-1,1-di(2-methoxyphenyl)-1-propanol,
(R)-N-(3-methoxysalicylidene)-2-amino-1,1-di(2-methoxyphenyl)-1-propanol,
(R)-N-salicylidene-2-amino-1,1-di(2-n-butoxy-5-tert-butylphenyl)-1-propanol,
(R)-N-(5-nitrosalicylidene)-2-amino-1,1-di(2-n-butoxy-5-tert-butylphenyl)-1-propanol,
(R)-N-(3,5-dinitrosalicylidene)-2-amino-1,1-di(2-n-butoxy-5-tert-butylphenyl)-1-propanol,
(R)-N-(5-chlorosalicylidene)-2-amino-1,1-di(2-n-butoxy-5-tert-butylphenyl)-1-propanol,
(R)-N-(3,5-dichlorosalicylidene)-2-amino-1,1-di(2-n-butoxy-5-tert-butylphenyl)-1-propanol,
(R)-N-(3-fluorosalicylidene)-2-amino-1,1-di(2-n-butoxy-5-tert-butylphenyl)-1-propanol,
(R)-N-(3-bromosalicylidene)-2-amino-1,1-di(2-n-butoxy-5-tert-butylphenyl)-1-propanol,
(R)-N-(3-methylsalicylidene)-2-amino-1,1-di(2-n-butoxy-5-tert-butylphenyl)-1-propanol,
(R)-N-(3-trifluoromethylsalicylidene)-2-amino-1,1-di(2-n-butoxy-5-tert-butylphenyl)-1-propanol,
(R)-N-(5-trifluoromethylsalicylidene)-2-amino-1,1-di(2-n-butoxy-5-tert-butylphenyl)-1-propanol,
(R)-N-(3-methoxysalicylidene)-2-amino-1,1-di(2-n-butoxy-5-tert-butylphenyl)-1-propanol,
(R)-N-(5-methoxycarbonylsalicylidene)-2-amino-1,1-diphenyl-1-propanol,
(R)-N-(2-hydroxy-1-naphtylidene)-2-amino-1,1-diphenyl-1-propanol,
(R)-N-(1-hydroxy-2-naphtylidene)-2-amino-1,1-diphenyl-1-propanol and the like, and compounds having (S)-configuration in place of (R)-configuration in the above exemplified compounds.

The above mentioned salicylaldimine compounds (1) may be produced, for example, by reacting an optically active amino alcohol (hereinafter, abbreviated as amino alcohol (2)) of formula (2):

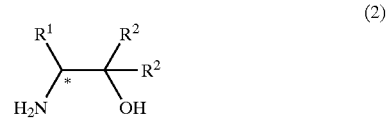

wherein $R^1$ and $R^2$ each have the same meanings as defined above, and the symbol * represents an asymmetric carbon atom, with an aldehyde compound (hereinafter, abbreviated as aldehyde compound (3)) of the following formula (3):

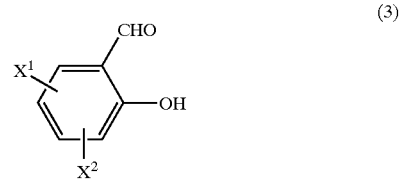

wherein $X^1$ and $X^2$ each have the same meanings as defined above.

Examples of the amino alcohol (2) include
(R)-2-amino-1,1-diphenyl-1-propanol,
(R)-2-amino-1,1-di(2-methoxyphenyl)-1-propanol,
(R)-2-amino-1,1-di(2-n-butoxy-5-tert-butylphenyl)-3-phenyl-1-propanol and compounds having (S)-configuration in place of the (R)-configuration in the above exemplified compounds.

Examples of the aldehyde compound (3) include, for example,
2-hydroxybenzaldehyde, 2-hydroxy-5-nitrobenzaldehyde,
2-hydroxy-3,5-dinitrobenzaldehyde,
2-hydroxy-5-chlorobenzaldehyde,
2-hydroxy-3,5-dichlorobenzaldehyde,
2-hydroxy-3-fluorobenzaldehyde,
2-hydroxy-3-bromobenzaldehyde,
2-hydroxy-3-methylbenzaldehyde,
2-hydroxy-3-trifluoromethylbenzaldehyde,
2-hydroxy-5-trifluoromethylbenzaldehyde,
2-hydroxy-3-methoxybenzaldehyde,
2-hydroxy-5-methoxycarbonylbenzaldehyde,
2-hydroxy-5-methoxycarbonylbenzaldehyde,
2-hydroxy-1-naphtoaldehyde and 1-hydroxy-2-naphtoaldehyde.

The aldehyde compound (3) is usually used in an amount range of 1 to 2 moles, preferably in the range of 1 to 1.5 moles per mol of the amino alcohol (2).

The reaction of the amino alcohol (2) and the aldehyde compound (3) can usually be conducted by simply mixing these compounds, and the reaction temperature is usually in the range of 20 to 150° C., preferably in the range of 50 to 120° C. The reaction is usually conducted in the presence of an organic solvent, and as such an organic solvent, aromatic hydrocarbon solvents such as toluene, xylene, benzene and halogenated hydrocarbon solvents such as chlorobenzene, chloroform, dichloroethane, and alcohol solvents such as methanol and ethanol maybe used alone or in combination. The use amount of the organic solvent is not particularly limited.

Since the reaction of the amino alcohol (2) with the aldehyde compound (3) usually proceeds almost quantitatively, the amino alcohol compound (1) can be used for the reaction with copper hydroxide (II) as it is without being extracted from the reaction solution, or the salicylaldimine compound (1) may be extracted from the reaction solution by concentration, followed by crystallization and/or the like operation, if necessary. Of course, the extracted amino alcohol compound (1) may be further purified by purification methods such as recrystallization or the like.

Next, a method of producing an optically active salicylaldimine copper complex by reacting the salicylaldimine, compound (1) with copper hydroxide (II) will be explained.

Copper hydroxide (II) may be used in powder form or in crystalline form or as a mixture thereof.

The copper hydroxide (II) is usually used in an amount of 0.9 to 1.5 moles, and preferably in an amount of 0.9 to 1.2 moles per mol of the salicylaldimine compound (1).

The reaction of the salicylaldimine compound (1) with the copper hydroxide (II) is carried out in an organic solvent. As the organic solvent, aromatic hydrocarbon solvents such as toluene and xylene, alcohol solvents such as methanol and ethanol, halogenated hydrocarbon solvents such as dichloromethane, chloroform, dichloroethane, and aliphatic hydrocarbon solvents such as hexane and heptane may be used alone or in combination. An optional amount of the organic solvent is used.

The reaction temperature is usually in the range of 20 to 150° C., and preferably in the range of 20 to 120° C.

The process for producing the optically active salicylaldimine copper complex of the present invention by reacting the salicylaldimine compound (1) with copper hydroxide (II) in the presence of the organic solvent can be conducted in the co-presence of water, thereby the yield can be improved. The amount of water is not particularly limited, however, 0.1 to 10 parts by weight per 1 part by weight of copper hydroxide (II) is preferred.

In accordance with the reaction, a reaction solution containing the optically active salicylaldimine copper complex is obtained. Although in the present reaction, water is formed as a byproduct from the reaction of copper hydroxide (II) with the amino alcohol compound, the obtained reaction solution containing the optically active salicylaldimine copper complex and water can be used as it is as a catalyst since water has nothing to do with the concerns of apparatus corrosion or harm to the reaction process and they are removed in the present process.

The reaction solution may be subjected to azeotropic distillation or treatment with a dehydration agent so as to remove the water. Alternatively, when water is separated from the reaction solution, the water may be removed by phase separation. The objective optically active salicylaldimine copper complex may be isolated, for example, by concentrating the reaction solution, and the isolated salicylaldimine copper complex may be further purified by a purification method such as recrystallization or the like, if necessary.

Examples of the optically active salicylaldimine copper complex include, for example:

[(R)-N-salicylidene-2-amino-1,1-diphenyl-1-propanol] copper complex,
[(R)-N-(5-nitrosalicylidene)-2-amino-1,1-diphenyl-1-propanol] copper complex,
[(R)-N-(3,5-dinitrosalicylidene)-2-amino-1,1-diphenyl-1-propanol] copper complex,
[(R)-N-(5-chlorosalicylidene)-2-amino-1,1-diphenyl-1-propanol] copper complex,
[(R)-(3,5-dichlorosalicylidene)-2-amino-1,1-diphenyl-1-propanol] copper complex,
[(R)-N-(3-fluorosalicylidene)-2-amino-1,1-diphenyl-1-propanol] copper complex,
[(R)-N-(3-bromosalicylidene)-2-amino-1,1-diphenyl-1-propanol] copper complex,
[(R)-N-(3-methylsalicylidene)-2-amino-1,1-diphenyl-1-propanol] copper complex,
[(R)-N-(3-trifluoromethylsalicylidene)-2-amino-1,1-diphenyl-1-propanol] copper complex,
[(R)-N-(5-trifluoromethylsalicylidene)-2-amino-1,1-diphenyl-1-propanol] copper complex,
[(R)-N-(3-methoxysalicylidene)-2-amino-1,1-diphenyl-1-propanol] copper complex,
[(R)-N-salicylidene-2-amino-1,1-di(2-methoxyphenyl)-1-propanol] copper complex,
[(R)-N-(5-nitrosalicylidene)-2-amino-1,1-di(2-methoxyphenyl)-1-propanol] copper complex,
[(R)-N-(3,5-dinitrosalicylidene)-2-amino-1,1-di(2-methoxy-phenyl)-1-propanol] copper complex,
[(R)-N-(5-chlorosalicylidene)-2-amino-1,1-di(2-methoxy-phenyl)-1-propanol] copper complex,
[(R)-N-(3,5-dichlorosalicylidene)-2-amino-1,1-di(2-methoxy-phenyl)-1-propanol] copper complex,
[(R)-N-(3-fluorosalicylidene)-2-amino-1,1-di(2-methoxy-phenyl)-1-propanol] copper complex,
[(R)-N-(3-bromosalicylidene)-2-amino-1,1-di(2-methoxy-phenyl)-1-propanol] copper complex,
[(R)-N-(3-methylsalicylidene)-2-amino-1,1-di(2-methoxy-phenyl)-1-propanol] copper complex,
[(R)-N-(3-trifluoromethylsalicylidene)-2-amino-1,1-di(2-methoxyphenyl)-1-propanol] copper complex,
[(R)-N-(5-trifluoromethylsalicylidene)-2-amino-1,1-di(2-methoxyphenyl)-1-propanol] copper complex,
[(R)-N-(3-methoxysalicylidene)-2-amino-1,1-di(2-methoxy-phenyl)-1-propanol] copper complex,
[(R)-N-salicylidene-2-amino-1,1-di(2-n-butoxy-5-tert-butyl-phenyl)-1-propanol] copper complex,
[(R)-N-(5-nitrosalicylidene)-2-amino-1,1-di(2-n-butoxy-5-tert-butylphenyl)-1-propanol] copper complex,
[(R)-N-(3,5-dinitrosalicylidene)-2-amino-1,1-di(2-n-butoxy-5-tert-butylphenyl)-1-propanol] copper complex,
[(R)-N-(5-chlorosalicylidene)-2-amino-1,1-di(2-n-butoxy-5-tert-butylphenyl)-1-propanol] copper complex,
[(R)-N-(3,5-dichlorosalicylidene)-2-amino-1,1-di(2-n-butoxy-5-tert-butylphenyl)-1-propanol] copper complex,
[(R)-N-(3-fluorosalicylidene)-2-amino-1,1-di(2-n-butoxy-5-tert-butylphenyl)-1-propanol] copper complex,
[(R)-N-(3-bromosalicylidene)-2-amino-1,1-di(2-n-butoxy-5-tert-butylphenyl)-1-propanol] copper complex,
[(R)-N-(3-methylsalicylidene)-2-amino-1,1-di(2-n-butoxy-5-tert-butylphenyl)-1-propanol] copper complex,
[(R)-N-(3-trifluoromethylsalicylidene)-2-amino-1,1-di(2-n-butoxy-5-tert-butylphenyl)-1-propanol] copper complex,
[(R)-N-(5-trifluoromethylsalicylidene)-2-amino-1,1-di(2-n-butoxy-5-tert-butylphenyl)-1-propanol] copper complex,
[(R)-N-(3-methoxysalicylidene)-2-amino-1,1-di(2-n-butoxy-5-tert-butylphenyl)-1-propanol] copper complex,
[(R)-N-(5-methoxycarbonylsalicylidene)-2-amino-1,1-diphenyl-1-propanol] copper complex,
[(R)-N-(2-hydroxy-1-naphtylmetylidene)-2-amino-1,1-diphenyl-1-propanol] copper complex,
[(R)-N-(1-hydroxy-2-naphtylmetylidene)-2-amino-1,1-diphenyl-1-propanol] copper complex and the like, and compounds of (S)-configuration corresponding to the above exemplified compounds of (R)-configuration.

The optically active salicylaldimine copper complex is suitably used in a cyclopropanation process, typically in a catalytic amount. Such process is usually conducted by reacting diazoacetic acid ester (e.g. lower alkyl ester such as methyl, ethyl or the like) with a prochiral olefin (e.g.

2-propene, 2,5-dimethyl-2,4-hexadiene and the like) in the presence of the optically active salicylaldimine copper complex to produce corresponding chiral cyclopropanecarboxylic acid ester.

EXAMPLES

In the following, the present invention will be explained more specifically by way of examples, however, the present invention is not limited to these examples.

Example 1

4.57 g of (R)-N-(5-nitrosalicylidene)-2-amino-1,1-di-(2-methoxyphenyl)-1-propanol and 1.02 g of copper hydroxide (II) were mixed in 50 g of toluene, and reacted under stirring for 1 hour at an internal temperature of 80° C., to obtain a toluene solution containing [(R)-N-(5-nitrosalicylidene)-2-]amino-1,1-di(2-methoxyphenyl)-1-propanol] copper complex. The solution was analyzed by a liquid chromatography, and the yield was 92.4%.

Example 2

4.57 g of (R)-N-(5-nitrosalicylidene)-2-amino-1,1-di(2-methoxyphenyl)-1-propanol, 1.02 g or copper hydroxide (II) and 0.99 g of water were mixed in 50 g of toluene, and reacted under stirring for 1 hour at an internal temperature of 80° C., to obtain a toluene solution containing [(R)-N-(5-nitrosalicylidene)-2-amino-1,1-di(2-methoxyphenyl)-1-propanol] copper complex. The solution was analyzed by a liquid chromatography, and the yield was 99.9%.

Production Example of Ethyl 3,3-dimethyl-2-(2-metyl-1-propenyl)cyclopropanecarboxylate To a 100 mL Schlenk tube purged with nitrogen, 33.06 g of 2,5-dimethyl-2,4-hexadiene and the toluene solution containing [(R)-N-(5-nitrosalicylidene)-2-amino-1,1-di(2-methoxyphenyl)-1-propanol] copper complex (copper complex content: 4.97 mg) obtained in the above Example 2 were added followed by 4 mg of phenylhydrazine, and then 1.14 g of ethyl diazoacetate was added dropwise over 2 hours at an internal temperature of 80° C. After completion of the dropwise addition, the resulting mixture was stirred for 30 minuets at the same temperature and reacted. As a result of an analysis by a gas chromatography, it was found that ethyl 3,3-dimethyl-2-(2-metyl-1-propenyl) cyclopropanecarboxylate was obtained in a yield of 97.1%, and the ratio of trans form /cis form was 59/41 (based on ethyl diazoacetate). Furthermore, liquid chromatography for determining optical purity showed an optical purity of 59% e.e. for trans form and an optical purity of 55% e.e. for cis form.

According to the present invention, an optically active saldoimine copper complex is obtained readily by reacting an optically active salicylidene amino alcohol compound with copper hydroxide (II) in an organic solvent, thereby undesirable byproduct that may inhibit the catalytic reaction or may corrode a reaction apparatus can be avoided.

What is claimed is:

1. A method for producing an optically active salicylaldimine copper complex, comprising reacting a copper hydroxide (II) with an optically active salicylaldimine compound of formula (1):

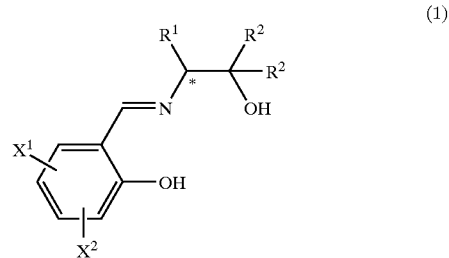

(1)

wherein $R^1$ and $R^2$ are the same or different and independently represent a substituted or unsubstituted lower alkyl group, a substituted or unsubstituted aryl group, or a substituted or unsubstituted aralkyl group, $X^1$ and $X^2$ are the same or different and independently represent a hydrogen atom, a substituted or unsubstituted lower alkyl group, a lower alkoxy group, a nitro group, a lower alkoxycarbonyl group or a halogen atom, and the symbol * designates an asymmetric carbon atom, provided that $X^1$ and $X^2$ on adjacent carbon atoms, together with the carbon atom to which they are boded form a benzene ring, in an organic solvent.

2. The method according to claim 1, wherein the organic solvent is toluene.

3. The method according to claim 1, wherein the reaction is carried out in the co-presence of water.

4. The method according to any one of claims 1 to 3, which further comprises the step of reacting a prochiral olefin with diazoacetic acid ester in the presence of the optically active salicylaldimine copper complex of claim 1 to produce a corresponding cyclopropanecatboxylic acid ester.

5. The method according to claim 4, wherein the prochiral olefin is 2-propene or 2,5-dimethyl-2,4-hexadiene.

* * * * *